(12) United States Patent
Bojanowski et al.

(10) Patent No.: US 10,398,490 B2
(45) Date of Patent: Sep. 3, 2019

(54) PROBE WITH GRIPPING STRUCTURE FOR ROBOTIC SURGICAL SYSTEM

(71) Applicant: Conmed Corporation, Utica, NY (US)

(72) Inventors: Michael Bojanowski, Denver, CO (US); Sachin A Sankholkar, Highlands Ranch, CO (US)

(73) Assignee: CONMED CORPORATION, Utica, NY (US)

( * ) Notice: Subject to any disclaimer, the term of this patent is extended or adjusted under 35 U.S.C. 154(b) by 533 days.

(21) Appl. No.: 14/878,356

(22) Filed: Oct. 8, 2015

(65) Prior Publication Data
US 2017/0007312 A1     Jan. 12, 2017

Related U.S. Application Data

(63) Continuation of application No. 29/532,410, filed on Jul. 7, 2015, now Pat. No. Des. 781,419.

(51) Int. Cl.
*A61B 18/04*     (2006.01)
*A61B 34/30*     (2016.01)
(Continued)

(52) U.S. Cl.
CPC ............ *A61B 18/042* (2013.01); *A61B 34/30* (2016.02); *A61B 34/35* (2016.02); *A61B 34/37* (2016.02);
(Continued)

(58) Field of Classification Search
CPC ........ A61B 18/042; A61B 2018/00589; A61B 2017/00477; A61B 34/30; A61B 34/35; A61B 34/37
See application file for complete search history.

(56) References Cited

U.S. PATENT DOCUMENTS 3,825,004 A * 7/1974 Durden, III ........ A61B 18/1402
                                                    138/106
3,853,111 A * 12/1974 Stanislawski ......... F41B 5/1469
                                                    124/35.2
(Continued)

FOREIGN PATENT DOCUMENTS

EP     0447121     9/1991
EP     2392278     12/2011

OTHER PUBLICATIONS

International Search Report of International Application No. PCT/US2015067566 dated Apr. 18, 2016.

*Primary Examiner* — Daniel W Fowler
(74) *Attorney, Agent, or Firm* — David L. Nocilly; Bond, Schoeneck & King, PLLC

(57) ABSTRACT

An argon beam coagulation probe for a robotic surgery system having a body with an argon gas entry port and an argon gas exit port and a pedestal interconnected to the underside of body that includes a pair of opposing arcuate channels that positioned equidistantly about the body. As a result, the argon gas jet exit port will be aligned equidistantly between the two fingers of a robotic arm and the body will be aligned in the same direction as the yaw axis of the robotic arm, so that argon gas will be expelled in the same direction that the fingers are pointing. A surgeon manipulating the robotic arms from the master control can thus easily align the probe based on the positioning of the robotic fingers and will still have the entire range of pitch, yaw, and roll movement of the robotic system.

6 Claims, 5 Drawing Sheets

(51) Int. Cl.
    *A61B 17/00* (2006.01)
    *A61B 18/00* (2006.01)
    *A61B 34/35* (2016.01)
    *A61B 34/37* (2016.01)
(52) U.S. Cl.
    CPC ............... *A61B 2017/00477* (2013.01); *A61B 2018/00589* (2013.01); *A61B 2034/302* (2016.02)

(56) References Cited

U.S. PATENT DOCUMENTS

| | | | | |
|---|---|---|---|---|
| 4,043,323 | A * | 8/1977 | Komiya | A61B 1/018 600/104 |
| 4,679,274 | A * | 7/1987 | Friedman | A46B 5/04 15/167.1 |
| 4,801,200 | A * | 1/1989 | Hussey | A61B 3/04 351/227 |
| 6,458,125 | B1 | 10/2002 | Cosmescu | |
| 2008/0058801 | A1 | 3/2008 | Taylor | |
| 2009/0125023 | A1* | 5/2009 | Stephen | A61B 18/042 606/42 |
| 2010/0234856 | A1 | 9/2010 | Stoianovici | |
| 2011/0092985 | A1* | 4/2011 | Gaynor | A61B 17/0482 606/139 |

* cited by examiner

PROBE WITH GRIPPING STRUCTURE FOR ROBOTIC SURGICAL SYSTEM

BACKGROUND OF THE INVENTION

1. Field of the Invention

The present invention relates to argon beam coagulation flex probes and, more particularly, and probe for use with minimally invasive robotic surgical systems.

2. Description of the Related Art

Minimally invasive robotic surgical systems, such as the da Vinci System available from Intuitive Surgical of Sunnyvale, Calif., have multiple robotic arms that can hold tools, such as scalpels, for manipulation by a surgeon using a set of master controls. The use of such system has expanded to include advanced surgical systems, such as ultrasonic scalpels, electrosurgical tools, and even fiber optic surgical systems that can be gripped by the robotic arms and then positioned by the surgeon for use. However, the manner in which these advanced surgical systems are coupled to the robotic system often obscures the surgical site and fails to preserve the high range of motion and alignment that is at the heart of the robotic systems. Accordingly, there is a need in the art for an argon beam coagulation probe that, when attached to a robotic surgical system, will allow a surgeon to properly manipulate, position, and use the probe.

BRIEF SUMMARY OF THE INVENTION

The present invention is an argon beam coagulation probe having a body extending along a longitudinal axis from a proximate end having an argon gas entry port to a distal end having an argon gas exit port and a pedestal interconnected to the body to define a pair of opposing channels positioned equidistantly about the longitudinal axis. The pedestal comprises a central member extending along a plane that encompasses the longitudinal axis and a pair of flanges extending from the central member opposite from the body. The body has a pair of shoulders spaced apart from the pair of flanges to define the two opposing channels. Preferably, each of the pair of channels are arcuate and include a first, longer portion at the proximate end of body and a second, short portion at the distal end of the body. The first, longer portion of each of the pair of channels extends toward the longitudinal axis from the proximate end of body to the distal end of the body. The second, shorter portion of each of the paid of channels extends away from the longitudinal axis from the proximate end of body to the distal end of the body.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
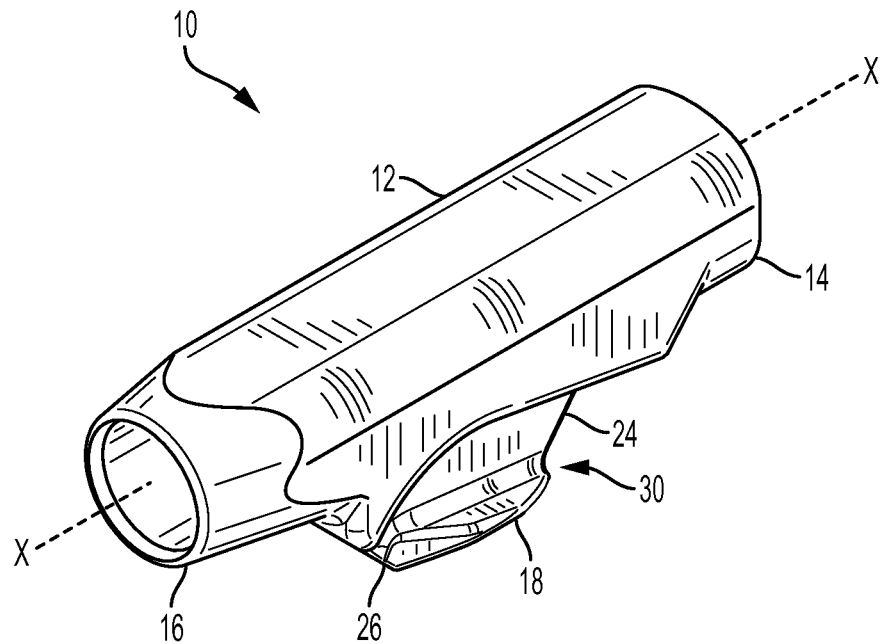
FIG. 1 is a perspective view of an argon beam coagulation flex probe for laparoscopic surgery according to the present invention.
Figure 2:
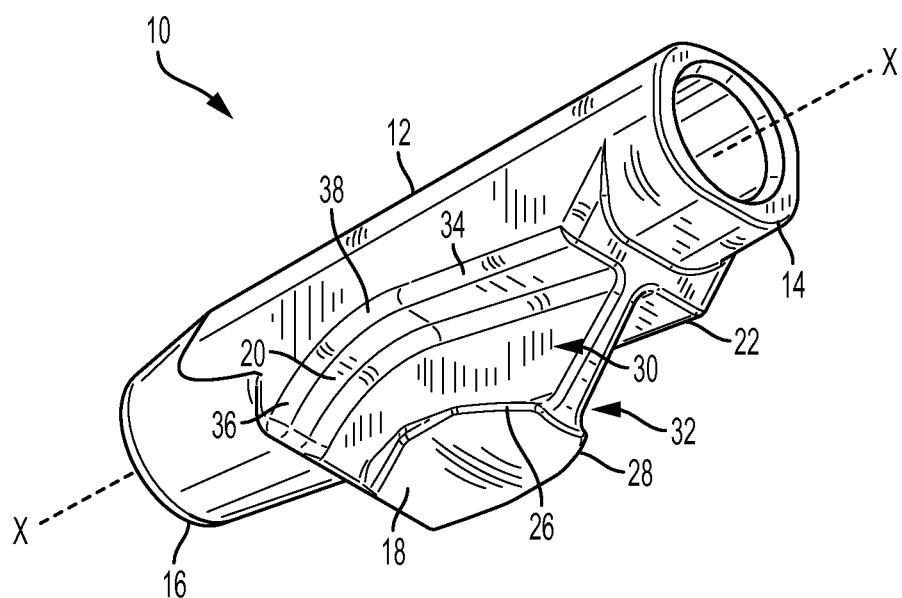
FIG. 2 is a second perspective view of an argon beam coagulation flex probe for laparoscopic surgery according to the present invention.

Referring now to the drawings, wherein like reference numerals refer to like parts throughout, there is seen in FIG. 1 an argon beam coagulation probe 10, such as one used with an argon beam coagulation system, that may be readily used by a robotic surgical system, including the da Vinci System. Probe 10 comprises a body 12 having from a proximal end 14 defining a supply port to which the source of argon gas and the internal electrode needed for an argon beam coagulation system may be attached or positioned within. Body 12 extends along a longitudinal axis X-X from proximal end 14 to an open distal end 16 from which the argon gas and plasma beam may be expelled onto tissue to be treated by the argon beam coagulation system. As seen in FIG. 2, distal end 16 can include a slight taper to assist in the flow of argon gas through and out of body 12, and to improve visibility of the tissue site around probe 10 when used with a robotic surgical system.

Referring to FIG. 2, body 12 includes a pedestal 18 positioned equidistantly between two shoulders 20 and 22 formed in body 12. Pedestal 18 extending outwardly from body 12 and includes a central member 24 that is attached to the underside of body 12. Central member 24 extends longitudinally along a portion of body 12 in a plane that intersects axis X-X. A pair of opposing flanges 26 and 28 extend outwardly from central member 24 to define, along with shoulders 20 and 22, a pair of opposing channels 30 and 32 that are positioned equidistantly about pedestal 18 on the underside of body 12, and thus equidistantly about axis X-X.

Figure 3:
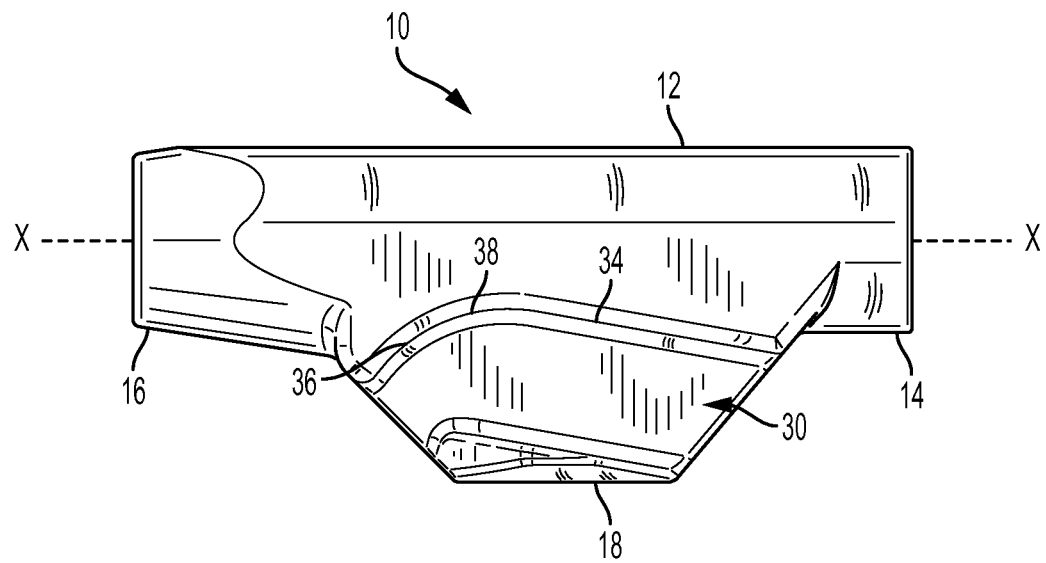
FIG. 3 is a left side view of an argon beam coagulation flex probe for laparoscopic surgery according to the present invention.
Figure 4:
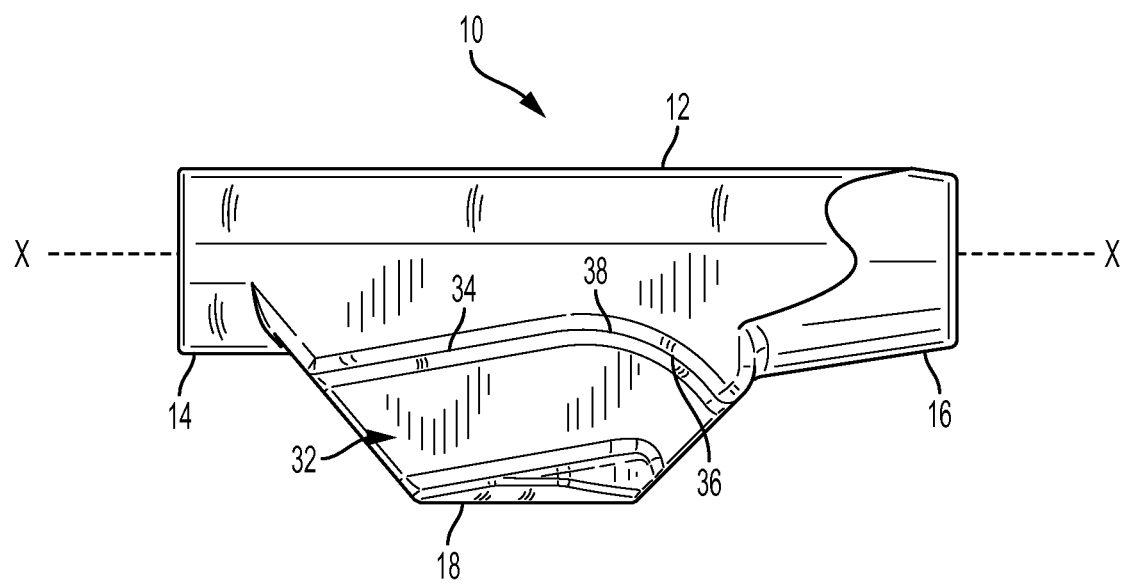
FIG. 4 is a right side view of an argon beam coagulation flex probe for laparoscopic surgery according to the present invention.
Figure 5:
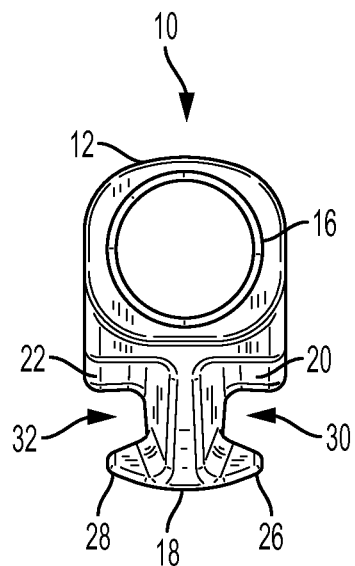
FIG. 5 is a front view of an argon beam coagulation flex probe for laparoscopic surgery according to the present invention.
Figure 6:
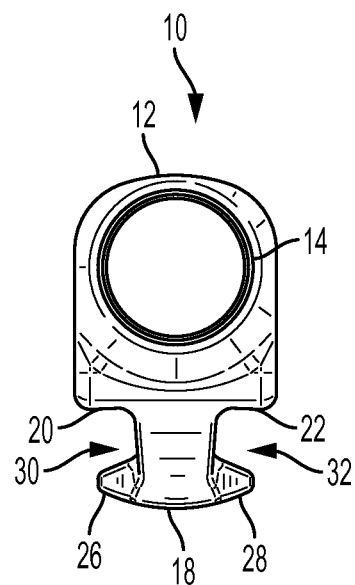
FIG. 6 is a rear view of an argon beam coagulation flex probe for laparoscopic surgery according to the present invention.
Figure 7:
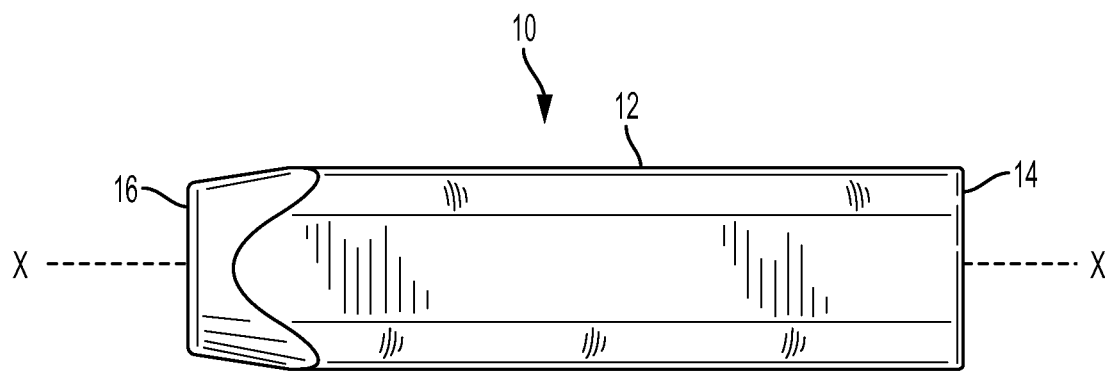
FIG. 7 is a top plan of an argon beam coagulation flex probe for laparoscopic surgery according to the present invention.
Figure 8:
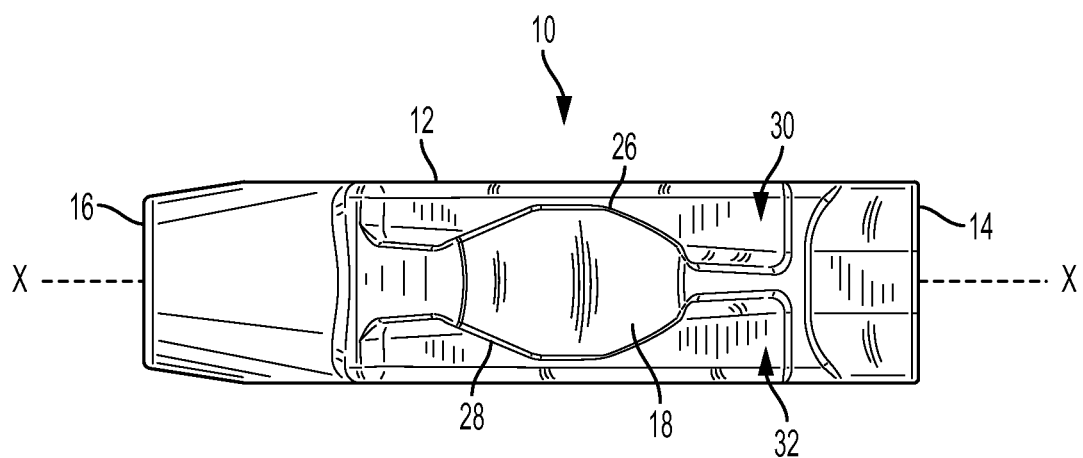
FIG. 8 is a bottom plan of an argon beam coagulation flex probe for laparoscopic surgery according to the present invention.

As seen in FIGS. 3 and 4, channels 30 and 32 extend along the underside of body 12. Channels 30 and 32 each include a first, linear portion 34 that extends toward axis X-X of body 12 and a second, arcuate 36 portion that extends from linear portion 34 away from axis X-X of body 12 to define a shoulder 38. Channels 30 and 32 are each adapted to receive a corresponding one of the two fingers of a robotic arm of a robotic surgical system so that each finger is captured within a respective linear portion 34 of one of channels 30 and 32, respectively. As seen in FIG. 8, channels 30 and 32 are slightly offset from axis X-X so that the proximal ends of channels 30 and 32 are closer together and to axis X-X while the distal ends are father apart to correspond to the geometry of robotic fingers 40 when they are closed from an open, V-shaped position into an almost fully closed grasping position to hold probe 10.

Figure 9:
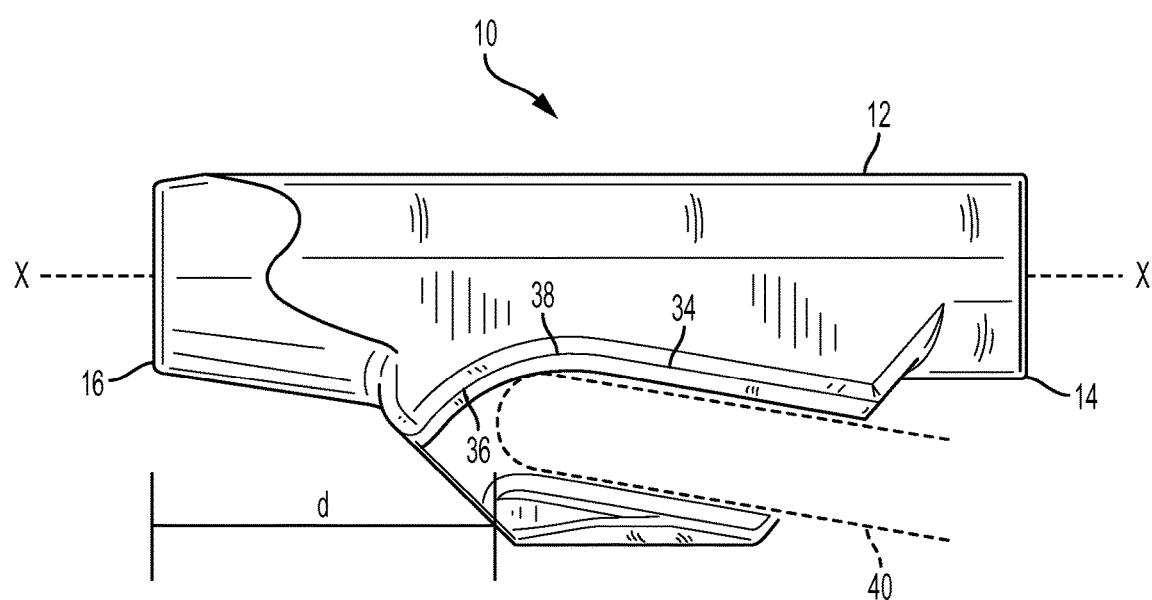
FIG. 9 is a left side view of an argon beam coagulation flex probe for laparoscopic surgery according to the present invention with robotic fingers shown in phantom.

Referring to FIG. 9, shoulder 38 formed by the overall arcuate shape of channels 30 and 32 assists in the retention of robotic fingers 40 within channels 30 and 32 by allowing each finger to be received in linear portion 34 with shoulder 38 of arcuate portion 36 acting as a stop to prevent further longitudinal movement of each finger 40 along body 12. Shoulder 38 is positioned and dimensioned to act as a stop that prevents the ends of each finger of the robotic arm from becoming too close to open distal end 16, which could lead to arcing between the energized argon plasma exiting open distal end 16 and fingers 40 of the robotic arm, which are typically metal. For example, in a body having a length of 0.500 inches+/−0.020, shoulder 38 may be configured to provide a setback distance "d" of 0.169 inches between open distal end 16 and the distal end of robotic fingers 40 of an exemplary robotic device, such as the da Vinci large needle driver (8 mm) available from Intuitive Surgical of Sunnyvale, Calif. The setback distance may be varied according to the size of body 12, the composition of robotic fingers 40, and the energy to be provided by probe 10. It should be recognized by those of skill in the art that shoulder 38 could instead be a protrusion or a wall at the end of liner portion 34, which would also act as stop preventing fingers 40 from becoming too close to open distal end 16. Shoulder 38 and arcuate portion 36 does allow probe 10 to be used with robotic fingers 40 having a curved or ovate shape, such as grasping forceps.

Referring to FIGS. 5-8, channels 30 and 32 are positioned equidistantly from axis X-X on either side of body 12 due to the positioning of pedestal 18 along a plane that intersects to axis X-X of body 12. As a result, distal end 16 of body 12 that provides the argon gas jet exit port will be aligned equidistantly between the two fingers of the robotic arm. In addition, axis X-X will be aligned in the same direction so the two fingers of the robotic arm, commonly referred to as the yaw axis of the robotic arm, so that argon gas will be expelled in the same direction that the fingers are pointing. As a result, a surgeon manipulating the robotic arms from the master control can easily align the argon gas stream existing probe 10 based on the positioning of the fingers. In addition, the alignment of axis X-X of probe 10 along the yaw axis of the robotic arm allows a surgeon to more easily transition probe 10 through the entire range of pitch, yaw, and roll movements that are the stated advantages of a robotic system having wrist-like movement capabilities.

What is claimed is:

1. An argon beam coagulation probe, comprising:
   a body extending along a longitudinal axis from a proximal end having an argon gas entry port adapted for connection to an argon beam coagulation system to a distal end having a taper than defines an argon gas exit port from which from argon gas and plasma beam may be expelled;
   a pedestal interconnected to the body and defining a pair of opposing channels that are positioned equidistantly about the longitudinal axis and that extend longitudinally under the body in an arcuate shape;
   wherein the pedestal comprises a central member extending along a plane that encompasses the longitudinal axis and a pair of flanges extending laterally from an end of the central member that is opposite the body and longitudinally along the body relative to the longitudinal axis; and
   wherein the body further comprises a pair of shoulders that extend longitudinally along the body relative to the longitudinal axis and are spaced apart from the pair of flanges to define the two opposing channels.

2. The probe of claim 1, where each of the pair of channels include a first, linear portion toward the proximal end of body and a second, arcuate portion toward the distal end of the body.

3. The probe of claim 2, wherein the first, linear portion of each of the pair of channels extends toward the longitudinal axis from the proximal end of body to the distal end of the body.

4. The probe of claim 3, wherein the second, arcuate portion of each of the pair of channels is curved away from the longitudinal axis from the proximal end of body toward the distal end of the body.

5. The probe of claim 4, wherein the arcuate portion defines a stop providing a predetermined setback distance between the argon gas exit port and the linear portion of the channel in which a robotic finger may be positioned.

6. The probe of claim 5, wherein the pair of channels are closer together and to the longitudinal axis toward the proximal end of the body than toward the distal end of the body.

* * * * *

UNITED STATES PATENT AND TRADEMARK OFFICE
CERTIFICATE OF CORRECTION

| | |
|---|---|
| PATENT NO. | : 10,398,490 B2 |
| APPLICATION NO. | : 14/878356 |
| DATED | : September 3, 2019 |
| INVENTOR(S) | : Michael Bojanowski and Sachin A. Sankholkar |

It is certified that error appears in the above-identified patent and that said Letters Patent is hereby corrected as shown below:

In the Claims

Column 4, Line 6, please change the word "than" to "that"
Column 4, Line 7, please change the word "from" between "which" and "argon" to "the"
Column 4, Line 25, please change the word "include" to "includes"
Column 4, Line 30, please add the word "the" between "of" and "body"
Column 4, Line 34, please add the word "the" between "of" and "body"

Signed and Sealed this
Thirteenth Day of August, 2024

Katherine Kelly Vidal
*Director of the United States Patent and Trademark Office*